(12) United States Patent
Avitall et al.

(10) Patent No.: US 6,171,237 B1
(45) Date of Patent: Jan. 9, 2001

(54) REMOTE HEALTH MONITORING SYSTEM

(76) Inventors: Boaz Avitall, 4868 N. Ardmore Ave., Milwaukee, WI (US) 53217; Brian Peterson, 2822 N. Frederick Ave., Milwaukee, WI (US) 53211; Joe Kletch, W. 165 N. 9744 Appleton Ave., Germantown, WI (US) 50322; Eric B. Griswold, 2578 N. Weil St., Milwaukee, WI (US) 53212; Patrick Moran, 2550 S. Brookland Rd., New Berlin, WI (US) 53151

( * ) Notice: Under 35 U.S.C. 154(b), the term of this patent shall be extended for 0 days.

(21) Appl. No.: 09/053,262

(22) Filed: Mar. 30, 1998

(51) Int. Cl.[7] .............................. A61B 5/00; A61B 10/00
(52) U.S. Cl. ......................... 600/300; 600/301; 128/920
(58) Field of Search .................................. 600/300, 301; 128/920, 903, 904, 905

(56) References Cited

U.S. PATENT DOCUMENTS

| | | | |
|---|---|---|---|
| 3,702,113 | 11/1972 | Blockley | 600/384 |
| 4,082,084 | 4/1978 | Lipscher | 600/513 |
| 4,695,955 | 9/1987 | Faisandier | 600/300 |
| 4,803,625 | 2/1989 | Fu et al. | 600/403 |
| 4,857,716 | 8/1989 | Gombrich et al. | 600/508 |
| 5,007,429 | 4/1991 | Treatch et al. | 600/490 |
| 5,341,291 * | 8/1994 | Roizen et al. | 600/300 |
| 5,348,008 | 9/1994 | Bornn et al. | 600/301 |
| 5,410,471 * | 4/1995 | Alyfuku et al. | 600/300 |
| 5,416,695 | 5/1995 | Stutman et al. | 600/300 |
| 5,435,315 | 7/1995 | McPhee et al. | 600/483 |
| 5,442,728 * | 8/1995 | Kaufman et al. | 600/300 |

\* cited by examiner

Primary Examiner—Max Hindenburg
Assistant Examiner—Navin Natnithithadha
(74) Attorney, Agent, or Firm—Gene Scott; Patent Law & Venture Group

(57) ABSTRACT

A computer control system operates with an instruction set to provide automated administration of health care to a patient. In a preferred embodiment of the invention a central monitoring station receives data from a plurality of remote testing units. Each of the testing units is custom configured for a particular patient and is made to provide optimal care for that individual alone. Similarly one monitoring unit may serve multiple patients and transmit the data to a central monitoring computer via the telephone lines. Medical procedures are then administered to the patient and results taken as data. The data is made available to the central monitor so that proper medical interpretation is enabled. A number of novel steps in the programming of the system are taken to assure that the right patient is being monitored, that the patient is being tested properly and that the system is being monitored appropriately.

22 Claims, 1 Drawing Sheet

REMOTE HEALTH MONITORING SYSTEM

This application is a substitute application of previously filed utility patent application 08/548,247 filed Oct. 25, 1995, now abandoned, this new application containing common matter therewith and new matter.

BACKGROUND OF THE INVENTION

I. Field of the Invention

The present invention is directed generally to a field of health care that involves monitoring the physiological state of patients with acute or chronic conditions or chronic disease states which predominantly derive decided prognosis advantages from intensive condition tracking. More particularly, the invention is directed to a condition monitoring system which includes one or more remote modular testing units and a central station. The remote units include physiological parameter testing modules to acquire data from one or possibly many patients and communicate with a central station typically capable of interfacing with a large number of patient-operated units or clinician-operated units testing many patients. The central station, in turn, may interface and communicate with any number of other devices as by networking. Parameters checked may include but are not limited to blood pressure, pulse rate, blood oxygen saturation, weight, blood glucose, temperature, prothrombin (clotting) time and pulmonary function, including respiratory rate and depth. Other functions, such as ECG (electrocardiograph) traces and infant breathing monitoring for detection of SIDS (sudden infant death syndrome) onset are also contemplated.

II. Related Art

Patients exhibiting any of a variety of serious, chronic conditions which require monitoring of medications, or the like, benefit from frequent testing. Many conditions which have traditionally required weekly or even daily clinic visits for testing may be tracked using remote monitoring with a customized testing frequency employed. This approach generally exceeds the benefits of care offered by frequent clinic visits at a fraction of the cost. In addition, hospital, assisted living and hospice units, for example, can also benefit greatly from portable, multiple-test patient monitoring units that monitor vital signs and conduct other tests and which are integrated into one management system including a central monitoring system capable of interfacing with many other devices.

An example of such a condition is congestive heart failure (CHE), a major public health concern, presently affecting 2 million patients within the United States. The problem is increasing and is responsible for over 1 million hospitalizations, with a typical length of stay of about six days, every year along with many physician visits. In addition, CHF commonly requires recurrent hospital admissions with 90-day readmission rates of over 50% reported in patients over the age of 70. Factors associated with high admission rates include inadequate follow up, failure of patients to promptly seek medical attention when symptoms recur, and non-compliance with diet and medication regimens. Much of this can be traced to the inadequacy of traditional home care, i.e., the lack of daily involvement of or interaction with the caregiver. The practicality of such situations invites inadequate monitoring of physiological parameters and a failure to appreciate and evaluate drug regimens which may result in inappropriate dosing or adverse side-effects or other problems.

The severity of CHF in an individual can further be evaluated and treatment updated quickly and in an ongoing manner by remote monitoring of several physiological parameters. The basic pathophysiology of CHF is reduced cardiac output usually with increased left ventricular filling pressures. An assessment of arterial pressure and pulse rates can indicate a failing heart. Typically, in patients with CHF, as stroke volume falls, resting heart rate increases. In addition, reduced cardiac output associated with increased pulmonary capillary wedge pressure leads to pulmonary edema and reduced systemic arterial oxygen saturation which is usually manifested as dyspnea by the patient.

Pulse oximetry is now a well-developed and widely used noninvasive technique of assessing oxygen saturation in pulmonary and cardiac patients. The valuable data obtained, including heart rate, has stimulated its use in acute, as well as chronic, care facilities treating pulmonary and cardiac diseases. Pulse oximetry can be used to indicate early signs of worsening cardiac failure if used to monitor patient desaturation during sleep. As left ventricular failure worsens, pulmonary congestion worsens and gas exchange is increasingly impaired, leading to a decrease in the arterial oxygen saturation as well as increase in heart rate. Timely reversal of this condition by relieving the left ventricle from excess afterload is essential and monitoring pulse oximetry also provides a measure of the improvements in cardiac output and reduction in left ventricular filling pressure that occurs with therapy.

Cardiac failure manifests itself by fluid retention and weight gain. Systemic venous congestion, another condition typical of CHF, is also reflected by salt and water retention which produces weight gain and an inappropriate increase in systemic blood pressure. Chronic systemic hypertension is also often the primary cause of failing heart and kidneys. Thus, closely monitoring patient weight also tracks the congestive state. Complementing this with blood pressure, heart rate and pulse oximetry monitoring provides the heath professional multiple objective measures.

Other such widespread chronic diseases or medical conditions include asthma, for example, for which pulmonary function is assessed by obtaining objective measurements of lung volumes and flow rates produced with maximum respiratory effort. These measurements are normally obtained using a spirometer, which measures vital capacity, tidal volume, expiratory reserve volume, and inspiratory capacity. Spirometry is an accepted, direct and sensitive measure of respiratory status that provides data for the direct assessment of current health status, disease exacerbation, compliance with prescribed drugs and drug efficacy.

Clinical experience has also shown that having patients perform Peak Expiratory Flow Rate (PEFR) measurements improves the clinician's ability to provide effective treatment.

Some reported uses of home PEFR are:

(1) monitoring to detect early airway obstructions and initiate timely therapy.
(2) monitoring the course of treatment, using objective criteria to alter steps in the treatment plan.
(3) determining when emergency medical care is needed.
(4) providing feedback to help patients perceive the severity of their obstruction.

Presently, PEFR is the only measurement obtained at home by patients using a Peak Flow Meter. However, the spirometer measures, along with PEFR, Forced Vital Capacity (FVC), Forced, Expiratory Volume at One Second ($FEV_1$), and Forced Expiratory Flow between 25% and 75% of the curve ($FEF_{25/75}$). These measurements require no additional effort by the patient yet they provide significantly more diagnostic information than the Peak Flow Meter.

Between 12 and 13 million people in the United States have diabetes mellitus and each year an additional 500,000 to 700,000 people are diagnosed with diabetes, of which 5% to 10% are diagnosed to have Insulin Dependent Diabetes Mellitus (IDDM). Patients diagnosed with IDDM must regularly inject themselves with insulin and monitor their blood glucose level with a glucose meter. A recent federal government study completed in 1993 has proven that lowering blood glucose levels to the normal range reduces the risk of major complications, such as blindness, kidney failure, heart attack or amputation and had reinforced the need for intensive management or close monitoring of diabetic patients. Intensive management may involve testing blood sugar level several times a day, at considerable expense and inconvenience, clearly avoidable by telecommunication glucose monitoring.

The above and other conditions reflect a growing need for remote patient monitoring. Some monitors have been developed for recording and transmitting certain patient-related information between remote locations and central stations or physicians, offices.

U.S. Pat. No. 4,803,625, issued to Fu et al, for example, discloses a portable patient unit connected to a central unit via a telephone line. The portable patient unit includes sensors for weight, temperature, blood pressure and ECG waveforms and may prompt the patient to take medicine, to use the sensors and to supply answers to various questions. The system allows communication between the patient unit and a central station and also can be used to query the patient where discrepancies between measured and expected values exist in the data.

U.S. Pat. No. 4,838,275, issued to Lee, which describes a home medical surveillance system that includes a large number of patient subscriber apparatuses that interface with a central station. Data is taken at a particular predetermined time and transmitted directly to the central station from the patient when taken. Parameters monitored may cover a broad spectrum and include blood pressure, heart rate, ECG, respiration rate and depth, center of gravity shifts, weight, temperature, breathing sounds, shivering, conversational characteristics, average blood glucose and relative cardiac output. The central office or station includes devices for transmitting/receiving interaction between the subscribers and the central station.

Gallant et al, U.S. Pat. No. 5,231,001, describes a microprocessor-based ambulatory patient monitoring system which may use a plurality of devices for measuring such parameters as ECG, blood pressure, oxygen saturation, temperature and respiratory function. Some degree of modularity is contemplated with the monitoring units. Data may be transmitted from the monitoring units over the telephone line to a PC. An optical interface may coordinate operation of one or more of the measuring units. The monitoring units may be coupled to a central computer system also utilized by the physician when particular patient information is relevant to identifying the patient and the data collected is relevant to any particularly measurement protocols, operating parameters and event triggering data.

U.S. Pat. No. 5,012,411, to Policastro et al, further describes a portable microprocessor-controlled apparatus for monitoring, storing and transmitting blood pressure, flow, and brain wave data from stored memory to a remote location over a telephone line or to a built-in graphic display or printer.

It remains, however, that the known remote patient monitoring devices or combinations of devices are relatively inflexible, generally dedicated to monitor particular conditions. They have varying degrees of portability and interface abilities both with the patient and with a remote monitoring station. There remains a definite need to provide a modular remote patient monitoring system which includes an interactive central station and self-contained mobile remote patient units, each of which can be tailored by the medical professional to perform measurements related to particular conditions applicable to each patient of interest. Interchangeable modular measurement parameter devices associated with a single, completely mobile patient monitoring unit adds a degree of control and flexibility not found in present systems.

SUMMARY OF THE INVENTION

The present invention provides a health monitoring system which includes one or more portable or mobile remote units and a main interface or central monitoring station. The remote units may be patient or clinician operated. In the patient-operated mode, the associated software interface is implemented to guide a patient through a coordinated test protocol, designed for a patient operated mode. A number of such remote units are distributed in patient homes, each monitoring an individual patient. The remote units collectively interface or are associated with a central monitoring station located at a care facility or other convenient location.

To the institutional environment, generally a single portable or mobile remote unit, programmed to be operated by a health professional, is used as a roving mobile unit to obtain physiological data from a number of patients. The data for many patients is transferred from the single mobile monitor to a central unit, possibly at a nursing station which, in turn, may be networked throughout the facility and any central station given the ability to communicate with as many other facilities as desired. This may include, for example, those patients serviced from a nursing station central to a wing of a floor in a hospital or other extended assisted care or assisted living facility.

A monitoring station is provided with an on-line data receiving modem and data processing and display systems which may include a personal computer (PC), a CRT display device, and a printer. The monitoring station receives, manages and stores patient data as transmitted from one or more remote units using telecommunication or other media. The monitoring station communicates with qualified health professionals who interpret and respond properly to the data from the patient or patients and may be linked or networked to access other clinics, hospitals, emergency response units or the like.

In the patient-operated mode each remote unit is a multi-parameter measuring and testing unit programmed for use by persons without medical training unassisted. Each instrument is a small portable or fully mobile device made up using a basic chassis or other basic unit into which a number of modular parameter measuring devices are assembled to provide a patient-customized system such that, whereas modules dedicated to measuring a variety of parameters are available, only those modules necessary to monitor the particular physiological parameters of interest for that patient need be included in a particular unit.

Each remote unit can be characterized as a basic data acquisition, processing, communicating and display system designed about a common bus interface unit permitting interface with a variety of self-contained instrument modules. Most or all of the modular physiological parameter measuring instruments that make up the input section or front end of the system are commercially available may be supplied by the same or by different OEMs (original equipment manufacturers). The units are prepared for internal incorporation in the remote monitor as necessary.

Modules included in remote units of the invention can be few or may be selected from modules to monitor blood oximetry, heart rate, blood pressure, weight, spirometry, blood glucose, temperature or possibly other modules including ECG monitors, respiratory monitors, including those for detecting SIDS in infants, prothrombin timing devices, etc. These devices can be combined into a portable, remote or mobile health monitor in any combination. In this respect, the remote health monitor of the invention is not a single device, but many, as the number of possible combinations of instruments and protocols is large.

The internal electronics of the remote unit includes the necessary circuit plug in receptacles and processing capability to accommodate any combination of front end or input test or measuring modules. This generally simplifies changing modules for individual patient units.

In the patient-operated mode, the remote unit communicates with the central monitoring station preferably via telephone lines but use with a wireless device, such as a cellular phone, or other communication mode is also contemplated. Incoming information from the remote monitor generally includes a patient ID number, date, and time data was collected together with the most recent physiological data obtained. Over time, the system compiles a relatively complete patient health record of data pertinent to the condition or disease of interest. Accumulated patient records can be printed, displayed in tabular or graphic form in a manner that allows analysis of time related trends on a monitor or printed format, data can be saved to diskette, or exported to other software or instrument or computer.

The remote unit and PC monitoring station preferably alert the users of both to significant deviations in physiological data obtained. Deviations from designed tolerance ranges may be used to trigger an alert or alarm condition. The remote unit may be programmed to alert the user directly as with a message and/or a beeping alarm and instruct the user to repeat the test for confirmation or to contact the physician. The data may then be automatically transmitted to the PC monitoring station where the software flags such a condition with a message box and continuous audio alert signal which can only be turned off by the intervention of a health professional.

In care facilities (clinician or professional-operated mode) the systems can update a patient's chart automatically and cause charts to be printed as desired. The remote unit may be custom programmed in correlation with each patient ID number so that a clinician can obtain the relevant data from each patient during rounds. In the clinician-operated mode, the remote unit may utilize the same operational menu structure as in patient-operated mode with an additional "Patient Select" menu. The Patient Select menu allows the clinician to select a patient from an internal list or selects the correct patient using a bar code reader. The health monitor is programmed with all patient names in the clinician routing.

A patient may be manually selected by scrolling through the programmed patient list and selecting the proper patient name. Likewise, tests may be manually selected by scrolling through the physiological parameter sub menus to select the tests to be performed. The parameter sub menu structure and all other underlying menu structures are the same menus used by the patient operator. The results of a test session are saved in the unit memory. Physiological data for all patients tested is stored within the health monitor memory. Safeguards may be implemented in the design and software to guard against patient data corruption. The patient information is then downloaded into the monitoring station and placed into patient-specific files. Data obtained from each patient can be viewed independently and can be viewed in a graphical trending form, tabular form or hardcopy tabular and graphics form. The same monitoring station can be used for tracking both inpatients and outpatients.

A cart may be provided for the organization of the health monitor, particularly the clinical version, and its peripheral sensors. The health monitor cart provides support and mobility to an instrument that facilitates collection of an array of physiological parameters. The health monitor cart may also carry an auxiliary power saver and carries the weigh scale stand. The cart is mounted on casters or wheels for mobility as in transfer from and to patient rooms. Padded handles that may be made conductive to obtain ECG data when gripped are included. A cantilever construction offers the patient further stability when the patient is on the weigh scale. The modular remote unit is easily attached and detached from an upper recess in the cart allowing for some tests to be conducted on patients without need for the entire cart.

BRIEF DESCRIPTION OF THE DRAWING

The accompanying drawing illustrates the present invention. In such drawing:

DETAILED DESCRIPTION OF THE INVENTION

Figure 1:
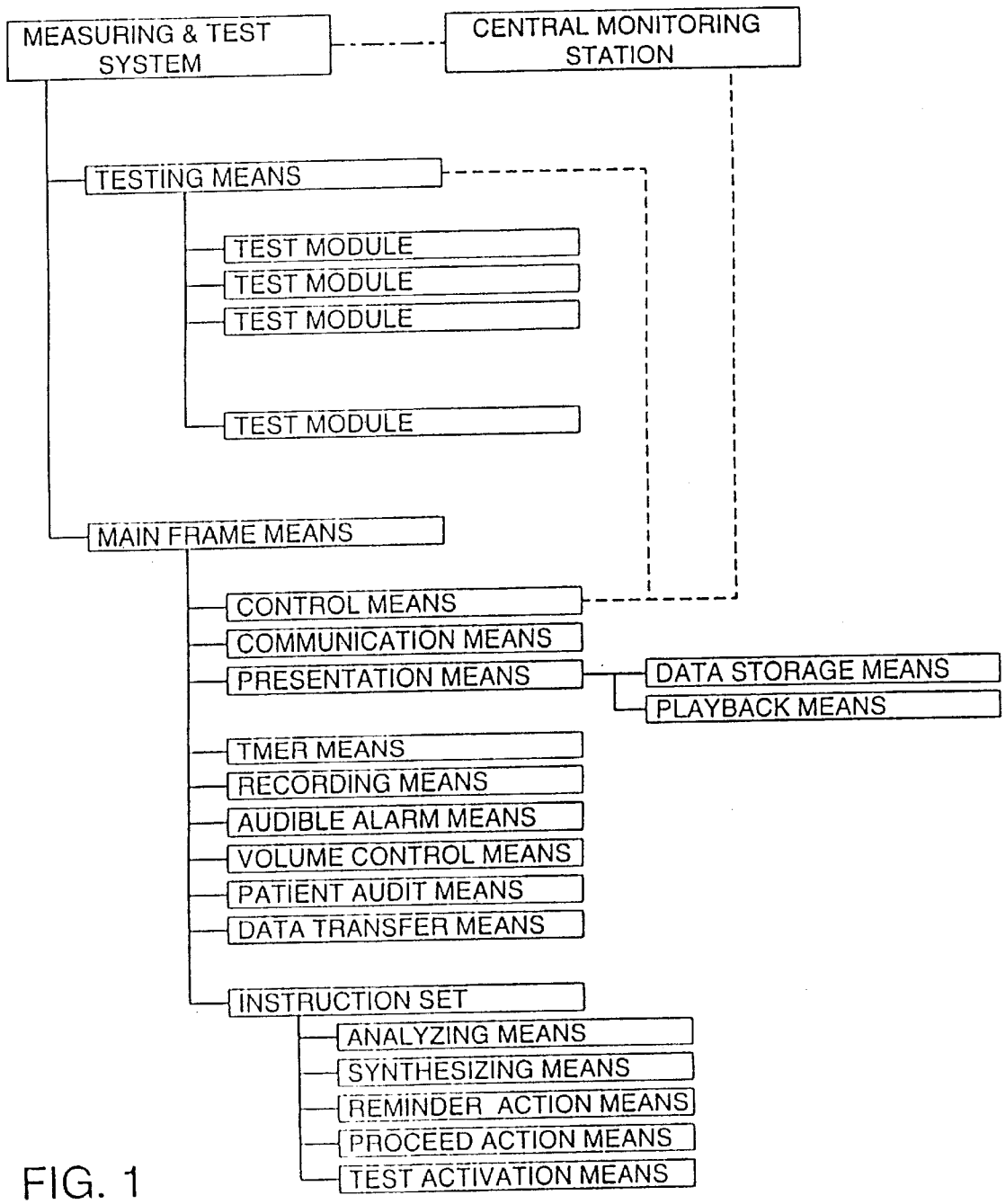
FIG. 1 is a diagram defining the important elements of the invention and their interrelationships where solid lines represent mechanical interrelationships, long-short dash lines represent modem or other wireless communication links, and uniformly dashed lines represent control relationships.

The above described drawing figures illustrate the invention, a measuring and testing system for automated administration of medical care to a patient, including communicating with a remote central monitoring station. FIG. 1 provides an overview of this system showing the relationship between the various elements, including mechanical, signal and control relationships. The measuring and testing system comprises a testing means and a main frame means as described further herein. The testing means is preferably a plurality of test modules, each of the modules enabling at least one medical procedure. The testing means therefore is able to be custom configured for each particular patient. The main frame means provides mechanical support to the testing means and further provides a programmable control means such as a microcomputer, electrically interconnected with the testing means for control thereof, a communication means such as a modem for enabling data transfer between the control means and the central monitoring station, and finally, a presentation means, such as a LCD or CRT display device, for audible and visual output message presentation to the patient. The presentation means provides a data storage means, such as a solid state memory device or a hard drive magnetic memory, for storing for playback, a plurality of reinforcement messages and a playback means, preferably employing a piezo crystal driver in a resonating enclosure, for playing the messages in response to patient actions. Such reinforcement messages enable the system-patient interface to improve and enable the patient to be motivated toward action improvement, i.e., more timely interface actions. The main frame means preferably also includes a timer means, such as a solid state timing circuit of any well known type, adapted for disabling the system after a preset operating duration and is further adapted to reset the system as directed by the control means in response to the central monitoring station. This feature is considered to be highly novel and inventive, and is important in assuring proper health care monitoring as well as building patient confidence in the system. The control means uses an instruction set (algorithm) in order to process the signals and data generated in the invention during operation. Such an instruction set is carefully crafted to carry out the objectives of the invention within the physical environment of the system and is well defined in accordance with industry practice so as to be easily made by those of skill in the art.

The mainframe means further preferably provides several features enabling a highly diversified capability with a broad range of applications. The hardware and processing programs to enable these capabilities are defined as follows:

A recording means, such as a solid state memory device, for recording patient test information, an audible alarm means such as a buzzer or bell, for alerting the patient to certain pre-selected conditions, and a volume control means, such as a potentiometer, for automatically increasing the volume of the audible alarm means until a manual reset action is taken. The algorithm provides an analyzing means (analysis logic), for analyzing the test information, a synthesizing means, for synthesizing a patient preferred test schedule according to preferred guidelines held in memory or downloaded as necessary, a reminder action means, for generating reminder actions based upon the test schedule, a proceed-action means for proceeding with a patient test only when a patient weight measurement is within a selected range, a test activation means for activating a patient test procedure based upon a patient test probe manipulation, a patient audit means for auditing patient compliance to an exercise regimen including repetitions of stepping onto a weight measuring means, or scale, so as to elevate heart rate and an automatic data transfer means for automatically downloading schedule information and uploading test results in accordance with the preferred embodiment of the method of the invention as described below. The means in the above cases are derived primarily from the programmed logic of the algorithm and as stated such means are generally well known as simple programming language manipulations. However, the combination of such means acting together in a system as defined herein is considered to be neither trivial nor of an obvious nature to those of skill in the art of programming and, as such, encompasses an important step in the field of the invention, i.e., the medical arts.

The invention teaches a method of remote measuring and testing for automated administration of medical care to a patient in accordance with the apparatus and program configuration described above. As defined herein the method comprises the steps of:

a) providing a measuring and testing system comprising a testing means and a main frame means, the testing means having a plurality of test modules, each of the modules enabling at least one medical procedure, while the main frame means provides mechanical support to the testing means;

b) controlling the testing means with a programmable control means electrically interconnected therewith;

c) transferring data with a communication means for enabling data transfer between the control means and the central monitoring station;

d) enabling the presentation of messages to the patient through a presentation means for audible and visual output from a storage means storing a plurality of reinforcement messages and a playback means for playing the messages in response to patient actions;

e) disabling the measuring and testing with a timer means adapted for disabling the system after a preset operating duration and further adapted to reset the system as directed by the control means in response to the central monitoring station; and f) disabling the system so as to require a purposeful action to reestablish operation assures the user that active monitoring is occurring so that confidence in the system and its valuable support to the patient continues to increase.

The method further provides for, recording patient test information, analyzing said test information, synthesizing a patient preferred test schedule, and generating reminder actions based upon the test schedule. Further, the method includes the step of proceeding with a patient test only when a patient weight measurement is within a selected range, so as to guard against the use of the system by an unauthorized person. Further certain tests may be activated based solely upon a patient test probe manipulation thereby simplifying the test for those with limited capabilities. The method may further include coordination of test alarm scheduling in conjunction with a television commercial schedule, so as to minimize the chance that the patient will be otherwise occupied when a test is called for. Further, the method may include coordination of test scheduling in response to predefined actions by the patient. If the system is placed in the bathroom, the auditory reminder for the patient to take measurements may be triggered when the patient flushes the toilet. Please note that in certain disease states such as congestive heart failure early morning post urination weight measurement is paramount for appropriate disease management.

The audible alarm means and a volume control means work together for automatically increasing the volume of the alarm until a manual reset action is taken thereby assuring that the alarm will be noticed by those with hearing problems while not becoming excessive for those without. Patient compliance to an exercise regimen including repetitions of stepping onto a weight measuring means which evaluates the number and the speed of the steps on the weight scale while assessing the heart rate and blood pressure. The exercise level of difficulty is calculated by assessing the double product of blood pressure and heart rate in relation to the number and speed of the steps onto the weight scale. The exercise routine is provided to the patient by the system display and the auditory tones that pace the patient to optimize the exercise level. Data is transferred between the measuring and test system and the central monitoring station by automatically downloading schedule information and uploading test results.

Further the method of the present invention may be described as a remote measuring and testing method for automated administration of medical care to a plurality of patients, the method comprising certain steps, preferably described as follows:

a) Providing a central monitoring station and a plurality of remotely located programmable patient care units as described above, one of the care units being assigned to each of the patients, wherein each of the care units enables at least one medical procedure for each patient, and preferably a range of procedures in accordance with each patient's medical needs.

b) Enabling data communication between the central monitoring station and each one of the patient care units.

c) Each of the patient care units being facilitated for storing and playing audible and visual patient messages; playing at least one of the patient messages in response to patient actions and, or inactions; disabling the patient care unit periodically after a preset operating duration; and resetting the patient care unit remotely from the central monitoring station.

This procedure has been described in detail above but it is preferred that the care units shall include at least one message of verbal praise, of pleasant tones, of short musical passages, of at least one inspirational saying, and a message describing patient compliance with test procedures. Certainly other messages of use may be included in the present invention message inventory within the spirit and use of the present invention method. The stored messages are selected to provide a range of behavior reinforcing strengths from strongly reinforcing to non-reinforcing, wherein each said played message may be selected at random from the inventory of stored messages. The purpose of this randomization is to impart the element of chance or variability to the procedure thereby enhancing operant conditioning. The direct comparison of the present device to a common slot machine is perhaps lacking in dignity and may account for the above objection: a more felicitous euphemism is here suggested. This is the same factor that makes games of chance intensely reinforcing, i.e., the variability of the payout schedule. Each one of the messages played is preferably constructed from a plurality of the messages stored so as to enable a larger vocabulary of played messages. This is possible by storing partial messages such that each partial message may be matched with one or more other of the partial messages to achieve each complete message. It is preferred also, in the present method to store patient data related to such areas as demographics, psychograpics, etc., and to derive the messages in accordance with said demographic data so as to correlate with it. This is easily accomplished by assigning factors of favorability to each of the messages as it relates to each possible one of the patient variables such as age, ethnic origin, sex, geographic origin, educational level and so on. Such a construction is easily programmed to make assignments so as to produce appropriate messages to each patient. In that the present invention includes a method of conditioning of the patient it is advantageous, whenever possible to provide messages that are intrinsically related to the conditioning process and particularly to the actions of the patient. As such, it is desirable to provide messages such as "You've had no alarms in over 5 days," and "Your weight is lower today than it was yesterday." Again, such messages may be easily stored as part of a standard message inventory which is programmed to be flagged for playout upon the occurrence of the appropriate series of patient related events.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A measuring and testing system for automated administration of medical care to a patient, including communicating with a remote central monitoring station, the measuring and testing system comprising:

a testing means comprising a plurality of separate testing modules, each of the modules enabling at least one medical procedure;

a main frame means mechanically supporting the testing means and further providing:
   a) programmable control means electrically interconnected with the testing means for control thereof;
   b) communication means for enabling data communication between the programmable control means and the central monitoring station;
   c) means for audible and visual output message presentation to the patient including a plurality of reinforcement messages and a means for playing the messages in response to patient actions the audible output means employing a piezo crystal driver in a resonating enclosure; and
   d) timer means adapted for disabling the system after a preset operating duration and further adapted to be reset through said data communication between the programmable control means and the central monitoring station.

2. The system of claim 1 further providing a means for recording patient test information, a means for analyzing said test information, and a means for synthesizing a patient preferred test schedule therefrom, and further, a means for generating reminder actions based upon the test schedule.

3. The system of claim 1 further providing a means for proceeding with a patient test only when a patient weight measurement is within a selected range.

4. The system of claim 1 further including a means for activating a patient test procedure solely through a patient test probe manipulation.

5. The system of claim 1 further including an audible alarm and a means for increasing the volume of the alarm until a reset action is completed.

6. The system of claim 1 further including a means for auditing patient compliance to an exercise regimen including repetitions of stepping onto a weight measuring means so as to elevate heart rate, the system providing the patient with auditory pacing rhythms to encourage the patient to follow a predefine exercise routine.

7. The system of claim 6, wherein an intensity of exercising is calculated using monitored heart rate, blood pressure and stepping rate.

8. The system of claim 6, further including means for automatically downloading schedule information and uploading test results.

9. A method for remote measuring and testing for automated administration of medical care to a plurality of patients, the method comprising the steps of:

a) providing a central monitoring station and a plurality of remotely located programmable patient care units, one of the care units being assigned to each of the patients, wherein each of the care units enables at least one medical procedure for a patient;

b) enabling data communication between the central monitoring station and each one of the patient care units, each of the patient care units:
   1) storing audible and visual patient messages, said messages including at least one of: a message of verbal praise, a message of pleasant tones, a message of short musical passages, a message of at least one inspirational saying, and a message describing patient compliance with test procedures;
   2) playing at least one of the patient messages in response to patient actions and inactions;
   3) disabling the patient care unit periodically after a preset operating duration; and
   4) resetting the patient care unit remotely from the central monitoring station.

10. The method of claim 9, wherein the stored messages of step (1) provide a range of behavior reinforcing strengths from strongly reinforcing to non-reinforcing, wherein each said message played in step (2) is selected at random from the stored messages.

11. The method of claim 9, wherein each one of the messages played in step (2) is constructed from a plurality of the messages stored in step (1) so as to enable a larger vocabulary of played messages.

12. The method of claim 9, wherein each of the messages played in step (2) is selected at random from the messages stored in step (1).

13. The method of claim 9, further including the step of storing patient demographic data and the still further step of deriving the messages of step (2) in accordance with said demographic data so as to correlate therewith.

14. The method of claim 9, further including the steps of recording patient test information, analyzing said test information, synthesizing a patient preferred test schedule therefrom and providing appropriate said patient messages related thereto.

15. The method of claim 9, further including the step of proceeding with a patient test when a patient weight measurement is within a selected range.

16. The method of claim 9, further including the step of activating a patient test procedure solely through a patient test probe manipulation.

17. The method of claim 9, further including the step of increasing the volume of an audible alarm until a reset action is completed by the patient.

18. The method of claim 9, further including the step of periodically exchanging data between the remote central monitoring station and each of the patient care units on a scheduled basis to assure network operating status.

19. The method of claim 9, further including the step of coordinating a test alarm schedule with a television commercial broadcast schedule.

20. The method of claim 9, further including the step of coordinating a test alarm schedule with an auditory or visual response of a specific patient habit.

21. The method of claim 20, wherein the auditory or visual response relates to the flushing of a toilet.

22. The method of claim 20, wherein the auditory or visual response relates to the switching of a light.

\* \* \* \* \*